(12) United States Patent
Abraham-Fuchs et al.

(10) Patent No.: US 7,359,806 B2
(45) Date of Patent: Apr. 15, 2008

(54) METHOD FOR CARRYING OUT QUALITY CONTROL ON AN ANALYTICAL PROCESS AND DEVICE FOR CARRYING OUT SAID METHOD

(75) Inventors: Klaus Abraham-Fuchs, Erlangen (DE); Michael Moritz, Mistelgau (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/535,134

(22) PCT Filed: Oct. 22, 2003

(86) PCT No.: PCT/EP03/11712

§ 371 (c)(1),
(2), (4) Date: Jan. 17, 2006

(87) PCT Pub. No.: WO2004/046993

PCT Pub. Date: Jun. 3, 2004

(65) Prior Publication Data

US 2006/0167830 A1    Jul. 27, 2006

(30) Foreign Application Priority Data

Nov. 18, 2002  (DE) ................................ 102 53 700

(51) Int. Cl.
G01N 31/00    (2006.01)
(52) U.S. Cl. ...................................... 702/31
(58) Field of Classification Search .................. 702/31, 702/12; 703/12
See application file for complete search history.

(56) References Cited

U.S. PATENT DOCUMENTS 5,307,262 A * 4/1994 Ertel .............................. 705/2
5,473,551 A   12/1995 Sato et al.
5,532,941 A   7/1996 Lin (Continued)

FOREIGN PATENT DOCUMENTS

DE    44 06 256 A1    9/1994

(Continued)

OTHER PUBLICATIONS

"Schlauer Blutsensor", von N. Aschenbrenner, Spektrum der Wissenschaft, Apr. 2002, Seiten 92 u. 93.

Primary Examiner—Michael P. Nghiem
Assistant Examiner—Xiuqin Sun
(74) Attorney, Agent, or Firm—Harness, Dickey & Pierce, PLC

(57) ABSTRACT

A method is proposed for carrying out quality control on an analytical process which belongs to a group of related analytical processes that can be executed in at least one analytical device and includes a respective chain of sub-processes. The method includes fundamental chemical and/or physical underlying sub-processes being stored for the group in a first database. Further, at least one section of the chain of the analytical process is emulated by the specification of one of the underlying sub-processes for each sub-process in a section of the chain, using at least one control parameter and at least one corresponding threshold value. Finally, measured values are determined for the control parameters for at least one run of the analytical process and the measured values are compared with the corresponding threshold values for the quality control procedure.

34 Claims, 2 Drawing Sheets

U.S. PATENT DOCUMENTS

| | | |
|---|---|---|
| 6,055,487 A | 4/2000 | Margery et al. |
| 6,055,587 A | 4/2000 | Asami et al. |
| 6,622,101 B1 | 9/2003 | Oechsner et al. |
| 2001/0043882 A1* | 11/2001 | Berger et al. .................. 422/67 |
| 2002/0116224 A1 | 8/2002 | Hengerer et al. |
| 2002/0133255 A1 | 9/2002 | Wardlaw et al. |
| 2003/0004696 A1* | 1/2003 | Yamazaki et al. ............ 703/12 |
| 2006/0149407 A1* | 7/2006 | Markham et al. ........... 700/108 |

FOREIGN PATENT DOCUMENTS

| | | |
|---|---|---|
| DE | 198 30 891 A1 | 1/2000 |
| EP | 0 359 049 A2 | 3/1990 |
| EP | 0 962 872 A2 | 12/1999 |
| EP | 0962872 | 12/1999 |
| EP | 1 145 088 A0 | 7/2000 |
| EP | 1 061 372 A2 | 12/2000 |
| EP | 1061372 | 12/2000 |
| EP | 1 107 159 A2 | 6/2001 |
| EP | 1107159 | 6/2001 |
| EP | 1145088 | 10/2001 |

* cited by examiner

METHOD FOR CARRYING OUT QUALITY CONTROL ON AN ANALYTICAL PROCESS AND DEVICE FOR CARRYING OUT SAID METHOD

This application is the national phase under 35 U.S.C. § 371 of PCT International Application No. PCT/EP2003/011712 which has an International filing date of Oct. 22, 2003, which designated the United States of America and which claims priority on German Patent Application number DE 102 53 700.3 filed Nov. 18, 2002, the entire contents of which are hereby incorporated herein by reference.

FIELD

The invention generally relates to a method of carrying out quality control for an analysis process which takes place in an analyzer and includes a chain of sub-processes, and/or to a device for carrying out the method. It relates in particular to quality assurance for biochemical analyzers, especially for medical diagnosis and particularly when using one of the technologies comprising biochips, "labs on the chip" and µTAS ("Totally Integrated Analysis Systems" involving microtechnology) as well as quality assurance for the manufacturing process of disposable sensors and other consumable articles used in the analyzer, such as reagent cartridges, sensors with limited life and maintenance-intensive components.

BACKGROUND

An analyzer which includes an evaluation device and blood-fillable thumbsize disposable sensors intended to be inserted into the evaluation unit is known, for example, from the article by N. Aschenbrenner "Schlauer Blutsensor" [smart blood sensor], Spektrum der Wissenschaft, April 2002, pages 92 and 93. Each of the disposable sensors furthermore comprises a chip which, inter alia, carries information for the analyzer concerning which special program should be run and how the evaluation should be carried out.

For the evaluation, a blood-filled disposable sensor is inserted into the evaluation unit, which then drives a pump in the disposable sensor that passes the blood over a membrane of the disposable sensor, which separates the blood red corpuscles, and delivers it into a chamber of the disposable sensor. Here, for example, the antigens that are contained in the blood and indicate a disease when they are in a high concentration react with specific color-labeled antibodies to form a complex. The mixture containing the complexes is furthermore sent by the pump onto a prism of the disposable sensor on which further antibodies are arranged, which capture and fix the complexes. Lastly, a laser of the evaluation unit then scans the prism and excites the color-labeled compounds to luminesce, and a detector of the evaluation unit picks up the fluorescent light, the intensity of the fluorescent light being a measure of the concentration of antigens.

According to the known methods, quality controls in biochemical analysis systems have to date been achieved by measurements of individual control values, measurements of reference analytes and random-sample comparative measurements with gold standard measuring methods. These methods, however, only offer conclusions about a few sub-processes of the analysis process and/or only provide integral information about a plurality of sub-processes together. Only information that the measurement is affected by error is usually possible, and conclusions cannot be drawn as to which sub-process is causing the error. Although this ensures reliability of the measurement results, it is of only very limited use for quality control in the manufacturing process of biochips or quality control in the maintenance process of an analyzer.

SUMMARY

It is an object of an embodiment of the invention to provide an improved method of carrying out quality control for an analysis process so that, inter alia, at least one of the aforementioned disadvantages are mitigated.

A method of at least one embodiment is for carrying out quality control for an analysis process, which belongs to a group of related analysis processes that can be carried out in at least one analyzer and respectively comprise a chain of sub-processes. The method includes:

fundamental chemical and/or physical basic sub-processes for the group are stored in a first database, at least a part of the chain of the analysis process is represented by specifying one of the basic sub-processes, per sub-processes of the part of the chain, using at least one control parameter and at least one associated threshold value, measurement values of the control parameters are determined for at least one run of the analysis process, and the measurement values are compared with the associated threshold values for the quality control.

In the analyzer, the analysis task is thus achieved by a sequence of sub-processes, each sub-processes being a chemical reaction, for example binding of two molecules, a physical reaction, e.g. heating, a transport procedure or mixing, or a physical measuring procedure. If even only one sub-processes is not carried out correctly then this generally indicates that the analysis result is affected by error, and the method detects this selectively for each of the quality-relevant sub-processes. An embodiment of the invention provides a generic quality control system using electronic databases, data inputs for process observation signals (control parameters) and software for evaluating the process quality from these observation signals, so that this quality control system can be used for any type of analysis systems or biochip technology and can be configured straightforwardly using a software user interface in order to be adapted for a specific analysis system or a specific biotechnology. This provides an automated quality control method which can be integrated into a biological analyzer, which cost-effectively assists the analyzer maintenance and which simultaneously provides information for quality assurance of the manufacturing process, for example of disposable sensors of the analyzer.

BRIEF DESCRIPTION OF THE DRAWINGS

Other advantages, features and details of the invention will be found in the example embodiments of the invention described below with reference to the figures, in which.

DETAILED DESCRIPTION OF THE EXAMPLE EMBODIMENTS

Figure 1:
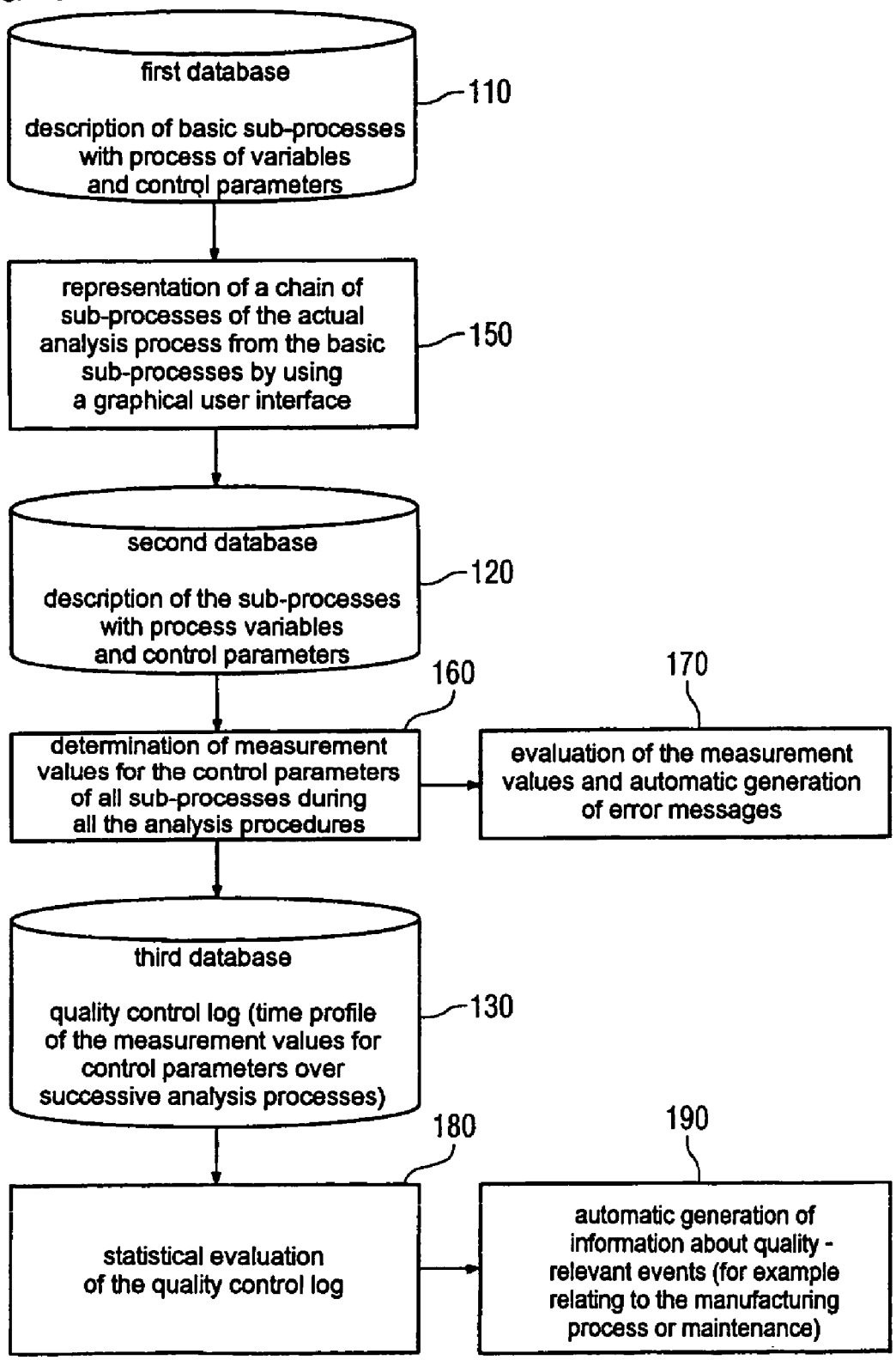
FIG. 1 shows a structural diagram and flow chart for a method of an embodiment of carrying out quality control for a biochemical analysis process.

As an example embodiment of the invention, FIG. 1 shows a structure and the procedure for a method of carrying out quality control for a biochemical analysis process which takes place in an analyzer and consists of a chain of sub-processes. For the quality control, there is a first database 110 in which all possible basic sub-processes of a group of related analysis processes are abstractly parameterized using process variables, and each of the basic sub-processes for the quality control can be characterized by at least one control parameter and by at least one threshold value in association with the control parameter.

Here, the basic sub-processes describe fundamental chemical and/or physical sub-processes of the group, and these fundamental sub-processes may occur repeatedly in modified forms throughout the analysis process. In this regard, the following table shows basic sub-processes A to F of the group by way of example with conceivable process variables associated with the individual basic sub-processes. For the respective basic sub-processes A to F, at least one control parameter is furthermore provided in the form of a substitute K(X), which should not lie below a lower threshold value min(X) and/or should not exceed an upper threshold value max(X) for the purpose of the quality control, X standing as a substitute for one of the basic sub-processes A to F. Without restriction of generality, an analyzer as described in the introduction should be thought of for better comprehension of the following table.

| Basic sub-process | Process type | Process variables | Control parameter | Lower threshold value | Upper threshold value |
|---|---|---|---|---|---|
| A | chemical binding | reagents; volumes; ... | K(A) | min(A) | max(A) |
| B | surface immobilization | capture molecule; target molecule; immobilization times; control substances; ... | K(B) | min(B) | max(B) |
| C | liquid transport | volumes; flow rates; transport times; ... | K(C) | min(C) | max(C) |
| D | mixing | mixing components; mixing times; | K(D) | min(D) | max(D) |
| E | demixing | mixing temperature; ... initial mixtures; target components; demixing times; demixing temperature; demixing medium; ... | K(E) | min(E) | max(E) |
| F | portioning | reagents; volumes; portioning media; ... | K(F) | min(F) | max(F) |

Starting with the basic sub-processes described in the first database 110, a second database 120 which compiles the actual analysis process of the analyzer from the basic sub-processes, and which describes it sufficiently completely, is generated in a first step 150 of FIG. 1. A suitable graphical user interface is used for this, which involves methods known from the prior art such as drag-and-drop, drop-down lists and/or checking list elements with a mouse click. For example, the chain of sub-processes is generated by dragging and dropping icons of the basic sub-processes, and the process variables and control parameters are established with the aid of selection from drop-down lists.

To this end, the analyzer includes a correspondingly designed computer workstation or is set up so that it can be connected to one. In some embodiments, the representation of the analysis process may be carried out at a central computer workstation with a corresponding graphical user interface, and the resulting database may be loaded in the scope of a manufacturing process of the analyzer into a memory intended for this in the analyzer, in which case the memory may even be a memory of disposable sensors of the analyzer, which can be put into a basic unit of the analyzer in order to carry out the analysis process.

For complete description of the timing sequence of the analysis process, each of the basic sub-processes contained in the first database 110 may occur repeatedly in the real process chain of the analysis process so that, if a basic sub-process occurs repeatedly, this sub-process should be labeled with a sequential number in the second database 120. The following table shows an example of this.

| Sub-process | Process type | Process variables | Control parameter | Lower threshold value | Upper threshold value |
|---|---|---|---|---|---|
| E1 | demixing | full blood as initial mixture; plasma as target component; demixing time | refractive index as K(E1) | min(E1) = 1.2 | — |
| B1 | surface immobilization | first antibody as capture molecule; antigen as target | first reference signal and as K(B1) | min(B1) = 0.4 | max(B1) = 0.9 |

-continued

| Sub-process | Process type | Process variables | Control parameter | Lower threshold value | Upper threshold value |
|---|---|---|---|---|---|
| C1 | liquid transport | molecule; control analyte as control substance storage volume and transport volume; transport time | conductance as K(C1) | — | max(C1) = 5.0 |
| F1 | portioning | portioning volume; piezoceramic as portioning medium | light absorption as K(F1) | min(F1) = 12.5 | — |
| A1 | chemical reaction | plasma and solution as reagents; portioning volume as reagent volume | temperature difference as K(A1) | min(A1) = 0.2 | — |
| D1 | mixing | antigen in portioning volume and magnetic beads as mixing components; mixing temperature | light absorption as K(D1) | min(D1) = 14.2 | max(D1) = 39.0 |
| E2 | demixing | portioning volume as initial mixture; magnetic field demixing medium; demixing temperature | magnetic field remanence as K(E2) | min(E2) = 240.0 | — |
| B2 | surface immobilization | fluorescent antibody as capture molecule; immobilization time | second reference signal and as K(B2) | min(B2) = 1 | max(B2) = 2 |
| C2 | liquid transport | portioning volume and surplus volume; transport time | refractive index as K(C2) | max(C2) = 1.15 | — |

The analysis process of the analyzer is thus described in the form of the second database 120, which contains all of the sub-processes E1 to D1 in their chronological order and associated characterizing features of the sub-processes. Preferably, it should not be necessary for the second database 120 to actually contain all the sub-processes of the analysis process that really occur, but only those which are in fact quality-relevant for an outcome of the analysis process.

During operation of the analyzer, observation signals for the control parameters K(E1) to K(C2) are determined by measurement in a second step 160, are stored in a further database, for example a third database 130, and are assigned to the corresponding control parameters K(E1) to K(C2). The measured observation signals may in this case also be assigned directly via a measurement value interface to the corresponding control parameters K(E1) to K(C2) of the second database 120. One of the observation signals may be a measurement value of a sensor or detector fitted in the analyzer, for example a temperature sensor, a photoelectric barrier or a photomultiplier, or it may be a value derived from one or more measurement values.

In a further step 170, in the course of each analysis procedure, the observation signals are evaluated and, in the event that a threshold value is infringed, error messages are automatically generated and reported on the analyzer. In the course of each analysis procedure, the measurement values for all the sub-processes are documented in the third database 130 and the reaching of a prescribed threshold value is evaluated, for example in the form of corresponding error flags being set. The following table shows an example of this, in which noncompliant mixing in the sub-process D1 is characterized by a "no" as the error flag since the measurement value of 7.9 lies below the lower threshold value min(D1).

| Sub-process | Carried out compliantly? | Measurement value for the respective control parameter |
|---|---|---|
| E1 | yes | 1.3 |
| B1 | yes | 0.45 |
| C1 | yes | 3.25 |
| F1 | yes | 24.9 |
| A1 | yes | 0.3 |
| D1 | no | 7.9 |
| E2 | ... | ... |
| B2 | ... | ... |
| C2 | ... | ... |

In other embodiments, the event of exceeding and/or lying below the threshold values may also be stored in the form of a percentage deviation in the third database 130. Furthermore, the analysis procedure may be terminated immediately with a corresponding error message on the analyzer if one of the control parameters K(E1) to K(C2) does not comply with one of the threshold values min(E1) to min(C2).

A time profile of the measurement values for the control parameters over successive analysis processes, for example with a plurality of a different disposable sensors, is finally stored in the third database 130 in the form of quality control logs. To this end, references of disposable sensors, references of disposable sensor batches and/or references of the individual analysis procedures are also stored in the third database 130.

In a further step 180, the third database 130, in which the measurement values for the control parameters K(E1) to K(C2) of many analysis procedures are stored over a predetermined period of time, may be evaluated by statistical methods. This is used in a further step 190 for the automatic generation of information about quality-relevant events, for example in order to draw conclusions about the analyzer from the variance of measurement values for at least one of the control parameters K(E1) to K(C2) over many analysis procedures, or from profile observation of measurement values for the control parameters in the scope of a trend, for example for necessary maintenance work. In an analyzer with disposable sensors, conclusions may furthermore be made about their production method, which is advantageous especially in conjunction with the provision of batch-specific control parameters.

The systematic procedure described above advantageously forces each analysis process to be examined rigorously in respect of quality-relevant sub-processes. If the analyzer is modified, other sub-processes can furthermore be added in a straightforward and rapid fashion, or existing sub-processes may be modified.

Figure 2:
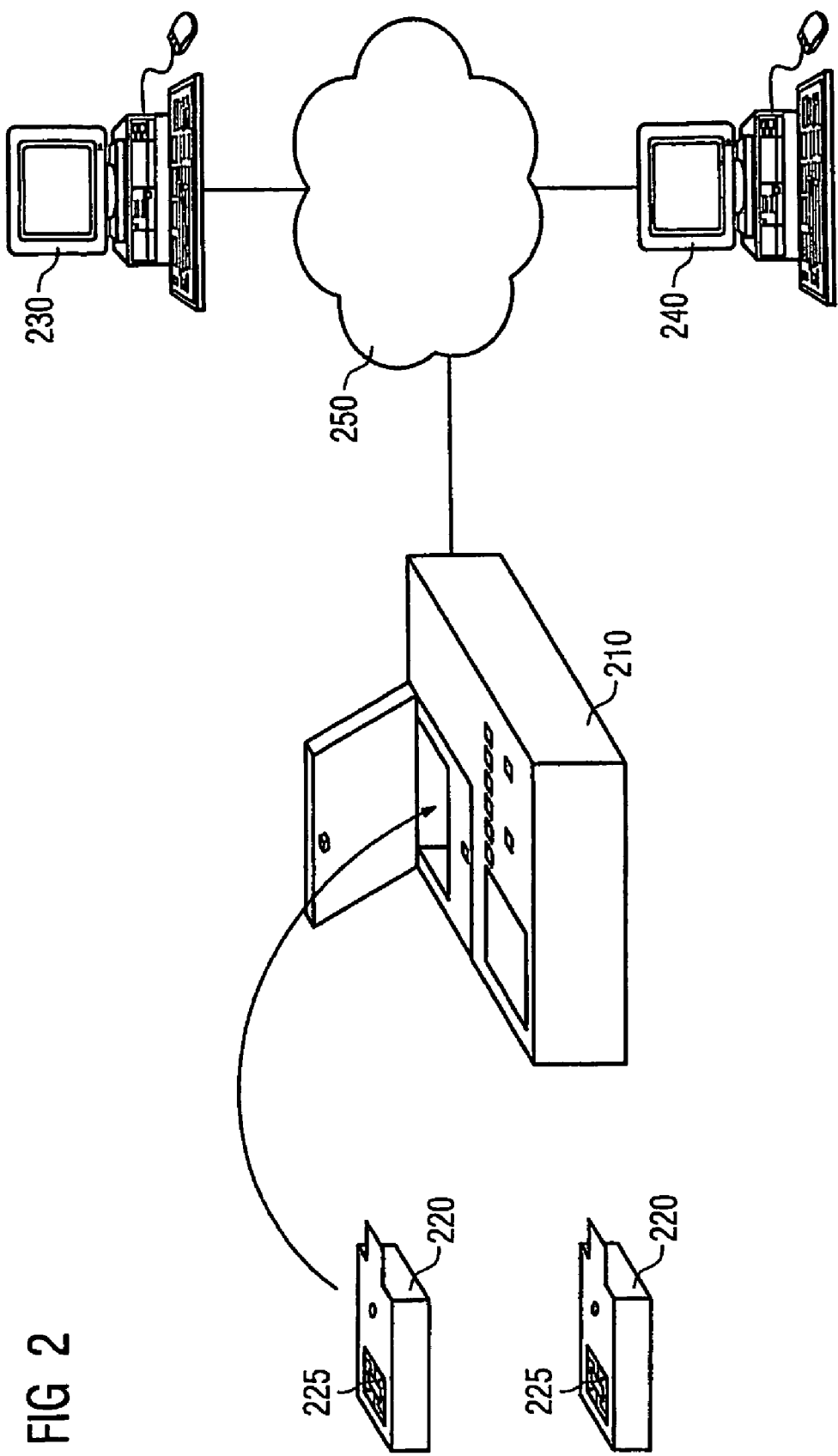
FIG. 2 shows an analyzer for carrying out the method of an embodiment, including an evaluation unit and disposable sensors which can be inserted into the evaluation unit.

As an example embodiment of the invention for carrying out the quality control method, FIG. 2 shows an analyzer which includes an evaluation unit 210 as a base unit and as subunits of the analyzer, for example, blood-fillable thumb-size disposable sensors 220 intended for insertion into the analyzer 210. Each of the disposable sensors 220 furthermore comprises a memory chip 225 which, inter alia, carries information for the analyzer 210 concerning which special program should be run and how the evaluation should be carried out.

The first database 110 may be stored either in the analyzer or on a computer workstation 230. To this end, the evaluation unit 210 is set up so that it can be connected via an electrically engineered data connection, especially the Internet 250, to a computer workstation 230. In another version, the evaluation unit 210 may even comprise a correspondingly designed computer workstation.

The process description specific to the analysis system is compiled from the basic sub-processes of the first database 110 on the computer workstation 230. The completed process description is then transferred from the computer workstation 230 to an electronic data memory in the analyzer, where it is stored as the second database 120. In one embodiment, the electronic data memory may even be a memory chip 225 accommodated on the disposable sensor 220. During the analysis procedures, the measurement values that are determined are likewise stored in the aforementioned data memory in the scope of the third database 130.

The evaluation of the measurement values saved in the third database 130 in the form of quality control logs is carried out automatically either in the analyzer or, preferably, on a further computer workstation 240 which has access to the databases 120 and 130 via an electrically engineered data connection, for example the Internet 250. Warning messages may be automatically generated and sent to the user and/or the manufacturer of the analyzer 210 or of the disposable sensors 220 when quality deficiencies are identified.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method of carrying out quality control for an analysis process of a group of related analysis processes including a chain of sub-processes, the method comprising:
   storing at least one of fundamental chemical and physical basic sub-processes for the group in a first database;
   representing at least a part of the chain of the analysis process by specifying one of the basic sub-processes, per sub-processes of the part of the chain, using at least one control parameter and at least one associated threshold value;
   determining measurement values of the control parameters for at least one run of the analysis process;
   comparing the measurement values with the associated threshold values for the quality control in a chronological order of the occurrence of the sub-processes in the part of the chain in the course of the analysis process; and
   outputting a result of the comparing the measurement values with the associated threshold values for the quality control.

2. The method as claimed in claim 1, wherein the analysis processes includes at least one of chemical and biochemical analysis processes.

3. The method as claimed in claim 1, wherein at least one of the basic processes is used repeatedly for the representation.

4. The method as claimed in claim 1, wherein the part of the chain contains only the quality-relevant sub-processes.

5. The method as claimed in claim 1, wherein the representation is aided by a correspondingly designed graphical user interface.

6. The method as claimed in claim 5, wherein the graphical user interface aids the representation by at least one of drag-and-drop techniques, drop-down lists and checking list elements with a mouse click.

7. The method as claimed in claim 1, wherein the represented part of the chain is stored with the control parameters and threshold values in a second database.

8. The method as claimed in claim 1, wherein associated measurement values lying above or below the threshold values are evaluated during the comparison.

9. The method as claimed in claim 1, wherein a run of the analysis process is terminated if one of the measurement values violates a predetermined relation with respect to the associated threshold value during the comparison.

10. The method as claimed in claim 1, wherein at least one of the measurement values and the results of the comparison are stored.

11. The method as claimed in claim 10, wherein a reference of a run of at least one of the analysis process and a reference of at least a part of an analyzer is also stored.

12. The method as claimed in claim 1, wherein at least one of the measurement values and the results of the comparison for a plurality of runs of the analysis process are at least one of stored and statistically evaluated.

13. The method as claimed in claim 1, wherein at least one of the measurement values and the results of the comparison are stored in a third database.

14. The method as claimed in claim 1, wherein at least one of the measurement values and the results of the comparison are used to at least one of assist maintenance of an analyzer for carrying out the analysis process and to provide feedback about a manufacturing processes of at least parts of the analyzer.

15. A device for carrying out the method as claimed in claim 1, the device comprising an analyzer for carrying out the analysis process.

16. The device as claimed in claim 15, wherein the device includes a computer workstation.

17. The device as claimed in claim 16, wherein the computer workstation is connectable to the analyzer.

18. The device as claimed in claim 17, wherein the analyzer and the computer workstation are connectable together via an electrically engineered data connection.

19. The device as claimed in claim 18, wherein the analyzer and the computer workstation are connectable together via the Internet.

20. The device as claimed in claim 16, wherein a first database is stored in the computer workstation.

21. The device as claimed in claim 16, wherein the computer workstation is designed for at least one of representing the part of the chain and for the statistical evaluation.

22. The device as claimed in claim 21, wherein at least one of a second database and at least parts of the third database are stored in the analyzer.

23. The device as claimed in claim 15, wherein the analyzer is designed for determining the measurement values.

24. The device as claimed in claim 15, wherein the analyzer includes a base unit and subunits, attachable into the base unit.

25. The device as claimed in claim 24, wherein the subunits are provided with an electronic memory chip.

26. The device as claimed in claim 25, wherein at least one of a second database and at least parts of the third database are stored in the subunits.

27. The device as claimed in claim 26, wherein a reference of the respective subunit are stored in the third database.

28. The device as claimed in claim 15, wherein the analyzer is intended for analyzing at least one substance in a bodily fluid of a living being.

29. The device as claimed in claim 15, wherein the analyzer includes a base unit and disposable, attachable into the base unit.

30. A device for performing an analysis process of a group of related analysis processes including a chain of sub-processes, the device comprising:

means for storing at least one of fundamental chemical and physical basic sub-processes for the group in a first database;

means for representing at least a part of the chain of the analysis process by specifying one of the basic sub-processes, per sub-processes of the part of the chain, using at least one control parameter and at least one associated threshold value;

means for determining measurement values of the control parameters for at least one run of the analysis process;

means for comparing the measurement values with the associated threshold values for the quality control in a chronological order of the occurrence of the sub-processes in the part of the chain in the course of the analysis process; and means for outputting a result of the comparing the measurement values with the associated threshold values for the quality control.

31. A device as claimed in claim 30, wherein the device includes an analyzer.

32. The device as claimed in claim 31, wherein the device includes a computer workstation.

33. The device as claimed in claim 32, wherein the computer workstation is connectable to the analyzer.

34. The device as claimed in claim 33, wherein the analyzer and the computer workstation are connectable together via an electrically engineered data connection.

* * * * *